United States Patent [19]

van Leeuwen et al.

[11] Patent Number: 4,467,116

[45] Date of Patent: Aug. 21, 1984

[54] PROCESS FOR THE HYDROFORMYLATION OF OLEFINS

[75] Inventors: Petrus W. N. M. van Leeuwen; Cornelis F. Roobeek, both of Amsterdam, Netherlands

[73] Assignee: Shell Oil Company, Houston, Tex.

[21] Appl. No.: 323,595

[22] Filed: Nov. 20, 1981

[51] Int. Cl.³ .............................................. C07C 45/50
[52] U.S. Cl. ..................................... 568/454; 568/909
[58] Field of Search ........................ 568/454, 909, 545

[56] References Cited

U.S. PATENT DOCUMENTS

| | | | |
|---|---|---|---|
| 3,917,661 | 11/1975 | Pruett et al. .......................... | 568/454 |
| 4,221,744 | 9/1980 | Unruh .................................... | 568/454 |
| 4,230,641 | 10/1980 | Bartish ................................. | 568/454 |
| 4,330,678 | 5/1982 | van Leeuwen et al. ............. | 568/454 |

FOREIGN PATENT DOCUMENTS

| | | | |
|---|---|---|---|
| 44-10765 | 5/1969 | Japan .................... | 568/454 |
| 48-40326 | 11/1973 | Japan .................... | 566/454 |

*Primary Examiner*—Werren B. Lone

[57] ABSTRACT

A process for the hydroformylation of less reactive olefins with hydrogen and carbon monoxide in the presence of a Group VIII-metal hydroformylation catalyst which has been modified by a ligand of formula $L(OR^1)(OR^2)(OR^3)$, wherein L represents P or As and $R^1$, $R^2$ and $R^3$ are similar or dissimilar aryl groups provided that at least one of $R^1$, $R^2$, $R^3$ is a group

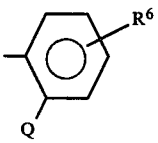

wherein Q represents a group

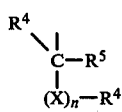

or a group

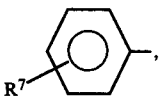

wherein $R^4$ is an optionally fluorine-substituted hydrocarbyl group, $R^5$ is H or $R^4$, $R^6$ is H or an inert substituent on the metal and/or the para position of the ring, X is O or S and n is 0 or 1 and $R^7$ represents a hydrogen atom or an inert substituent. Less reactive olefins such as limonene can be hydroformylated with very good results.

23 Claims, No Drawings

PROCESS FOR THE HYDROFORMYLATION OF OLEFINS

FIELD OF THE INVENTION

The present invention relates to a process for the hydroformylation of olefins using a modified Group VIII-metal catalyst.

BACKGROUND OF THE INVENTION

It is known that the hydroformylation reaction can be performed with good results using catalysts which comprise a Group VIII-metal compound which also contains a phosphorus or arsenic moiety. In general, preference is given to the use of phosphorus compounds, especially of trialkyl or triarylphosphines or phosphites as ligands in the catalytic hydroformylation of olefins.

It should be noted, however, that there is a vast difference in reactivity between various olefins under similar reaction conditions using an identical catalytic system. It is also known that the organo-phosphorus ligands may exert a distinct influence on the selectivity of the hydroformylation reaction when the same olefin is applied as the substrate. For instance, it is known from the article by Pruett and Smith (J. Org. Chem., Vol. 34, (1969), No. 2, pp 307-330) that in the hydroformylation of oct-1-ene with trisubstituted phosphorus-containing ligands, an aliphatic substituent gives a lower percentage of straight-chain (or normal) aldehdye than an aromatic substituent. However, the selectivity between various aromatic ligands, phosphines as well as phosphites does not seem to differ markedly. From British Pat. No. 1,325,199 it appears that the hydroformylation of hex-1-ene using a rhodium catalyst modified with various aromatic phosphites gives about the same yield and selectivity whereas the conversion using a catalyst comprising the unsubstituted aromatic phosphite, i.e. triphenylphosphite, is at least 10% higher.

It has now been found that a certain class of olefins which can be regarded as markedly less reactive olefins compared with olefins such as oct-1-ene and hex-1-ene can be hydroformylated at high rates and with good selectivity using Group VIII-metal catalysts modified with specific aromatic phosphites.

SUMMARY OF THE INVENTION

The present invention relates to a process for the hydroformylation of olefins which comprises reacting an olefin containing the group

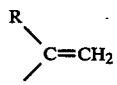

or the group

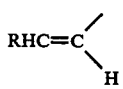

where in R represents a hydrocarbyl group and the valence bond shown forms part of a hydrocarbyl group, or R together with the valence bond shown represents a ring structure having at least 5 carbon atoms in the ring, with carbon monoxide and hydrogen in the presence of a Group VIII-metal hydroformylation catalyst which has been modified by a ligand according to the general formula $$L(OR^1)(OR^2)(OR^3)$$

wherein L represents a phosphorus or arsenic moiety and $R^1$, $R^2$ and $R^3$ represent (dis)similar aryl groups provided that at least one of $R^1$, $R^2$ and $R^3$ represents a group

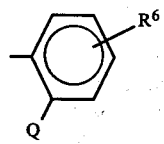

wherein Q represents a group

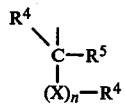

or a group

wherein each $R^4$ which may be the same or different represents an optionally fluorine-containing hydrocarbyl group, $R^5$ represents a hydrogen atom or a group $R^4$, and $R^6$ represents a hydrogen atom or an inert (to the hydroformylation reaction) substituent on the meta and/or para position of the ring, while X represents an oxygen or sulphur atom and n is 0 or 1, and $R^7$ represents a hydrogen atom or an inert (to the hydroformylation reaction) substituent.

DESCRIPTION OF THE PREFERRED EMBODIMENTS

Examples of a class of olefins containing a group

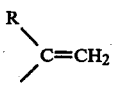

or

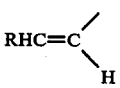

in the molecule which can be suitably used as starting materials in the process according to the present invention comprise β-alkyl-substituted acyclic α-olefins such as 2-methylbut-1-ene, 2-methylpent-1-ene, 2-methylhex-1-ene, 2-ethylhex-1-ene, 2,3-dimethylbut-1-ene, 2,3-dimethylpent-1-ene, 2,3,3-trimethylbut-1-ene, 2,3-dimethylhex-1-ene, 2,5-dimethylhex-1-ene, 2-ethyl-3-methylpent-1-ene, 2,6-dimethylhept-1-ene as well as β-alkyl-substituted α-olefins which contain a further β-substituted double bond such as 2,4-dimethylbutadiene-1,4 and isononadiene (2,6-dimethylheptadiene-1,5). The latter compound is of interest as a starting material for citronellal. Good results have been obtained using 2-methylhex-1-ene or 2-methylhept-1-ene as the starting olefins.

Another class of olefins which can be used suitably comprises β-alkyl-substituted α-olefins which contain also a cyclic structure in the molecule which may or may not contain additional double bonds. Examples of such compounds comprise isopropenyl cyclopentane, isopropenyl cyclohexane, isobutenyl cyclopentane, isobutenyl cyclohexane, isopropenyl benzene (α-methyl styrene) and isobutenyl benzene as well as isoalkenyl cycloalkenes provided the double bond in the ring structure comprises at least a lower alkyl group such as limonene (1-methyl-4-isopropenyl cyclohexene-1). Also compounds comprising a further β-substituted double bond such as 1,4-diisopropenyl cyclohexane can be used. If desired the ring structures may be substituted by one or more inert substituents such as fluorine, chlorine or alkyl groups as well as hydroxy groups not connected to or neighboring a carbon atoms forming part of a double bond. Typical examples comprise 1-isopropenyl-4-chlorocyclohexane and plinol (1-isopropenyl, 2,3-dimethyl-3-hydroxycyclopentane). Preferred as starting materials are the isopropenyl cycloalkanes and cycloalkenes, especially limonene.

A further class of olefins which can be used suitably comprises cyclic olefins having either a methylene group in the molecule or an unsubstituted double bond in the molecule. Examples of such olefins comprise methylenecyclopentane, methylenecyclohexane, cyclopentene, cyclohexene, cyclooctene, 1,4-dihydronaphthalene, 1,2-dihydonaphthalene, 1,2-dehydroindane, 2,3-dehydroindane, 6,7-dihydro-5H-benzocycloheptene and 8,9-dehydro-5H-benzocycloheptene. Good results have been obtained using methylenecyclohexane and cyclohexene.

The process according to the present invention is carried out in the presence of a modified Group VIII-metal catalyst. Suitable Group VIII-metals comprise rhodium and iridium, preference being given to the use of rhodium as the Group VIII-metal in the hydroformylation catalyst. The amount of catalyst may vary within wide ranges, but generally the molar ratio of catalyst to olefin is in the range of from 1:10000 to 1:10, preferably between 1:5000 and 1:100.

The modified catalyst comprises a complex of a Group VIII-metal, carbon monoxide, an organic ligand, especially a phosphite as defined hereinbefore and an anion to match the neutrality of the catalytic species. The catalyst can be prepared as such but it may also be formed in situ under the prevailing reaction conditions. Suitable starting materials comprise monovalent rhodium or iridium salt such as 1,5-cyclooctadiene rhodium(I) acetate and 1,5-cyclooctadiene rhodium(I) chloride. Chloride-containing starting materials are preferably first treated with a chloride acceptor.

As discussed hereinbefore, at least one of the groups $R^1$, $R^2$ and $R^3$ in the phosphite $L(OR^1)(OR^2)(OR^3)$ represents a specific ortho-substituted phenyl group. The nature of this group is rather critical with respect to the hydroformylation of less reactive olefins. It has been found that the use of tris-o-tolylphosphite gives only a very slow initial rate in the hydroformylation of 2-methyl-1-ene comparable with the yield obtained by using the well-known ligand triphenylphosphine and that no product could be found at all when tris-2,6-dimethylphenylphosphite was used as the phosphorus ligand under the reaction conditions according to the present invention.

Preference is given to the use of phosphites according to the general formula $L(OR^1)(OR^2)(OR^3)$ wherein the groups $R^1$, $R^2$ and $R^3$ are identical, but dissimilar groups can also be used suitably. Examples of ortho-substituted phenyl groups which can be suitably used comprise those wherein $R^4$ represents a lower alkyl group, $R^5$ represents a hydrogen atom or a lower alkyl group, $R^6$ represents a hydrogen atom, a fluorine or chlorine atom, an alkyl or alkoxy group and n is 0 or 1 in which case X represents an oxygen or sulphur atom, and $R^7$ represents a hydrogen, fluorine or chlorine atom or a lower alkyl or alkoxy group. Preference is given to the presence of ortho-substituted phenyl groups wherein $R^4$ represents a methyl or ethyl group. $R^5$ represents a hydrogen atom or a methyl group, $R^6$ represents a hydrogen atom or methyl or ethyl group and n is 0 and $R^7$ represents a hydrogen atom. Very good results have been obtained using tris(2-t.butylphenyl)phosphite or tris(2-t.butyl-4-methylphenyl)phosphite as the phosphorus ligand in the hydroformylation of various less reactive olefins, especially cyclohexene, limonene and methylenecyclohexane.

The process accoring to the present invention is preferably conducted in the presence of an excess of the phosphite having the general formula $L(OR^1)(OR^2)(OR^3)$ since such excess exerts a beneficial effect on the catalytic activity. Normally, metal-phosphorus ratios of from about 1:2 to about 1:100 can be used, preference being given to ratios in the range of from about 1:4 to about 1:20.

Generally, the hydroformylation of the olefins as defined hereinbefore is carried out under rather mild conditions. Temperatures in the range of from about 50° C. to about 200° C. can be suitably applied, preference being given to temperatures in the range of from about 80° C. to about 130° C.

The pressure, which is the sum of the hydrogen and carbon monoxide pressure, is suitably in the range of from about 2 to about 50 bar, preferably between about 3 and about 35 bar, although lower or higher pressures are not excluded. Generally, the molar ratio of hydrogen to carbon monoxide is in the range of from about 1:2 to about 12:1. Good results have been obtained using hydrogen and carbon monoxide in equimolar as well as in about 2:1 molar ratios.

The process according to the present invention may be conducted in the presence of an inert solvent. Examples of suitable solvent comprise saturated hydrocarbons such as pentane, hexane and higher alkanes, naphtha, kerosene, mineral oil, cyclopentane and cyclohexane, as well as the aromatic hydrocarbons such as benzene, toluene and the xylenes as well as ethers, ketones and nitriles. Also mixtures of solvents can be suitably applied. It is also possible to use an excess of the starting material as solvent.

The process according to the invention can be readily carried out using well-known chemical engineering practice which includes continuous, semi-continuous and batch operation. The reaction time may vary between wide limits, from a couple of minutes to several hours depending on the specific olefin and phosphite applied. After the reaction, the reaction mixture is worked up by techniques known in the art. The product aldehyde can be recovered by various means, e.g. by distillation. It is also possible to recycle part or all of the catalyst and the remaining reaction mixture.

The invention will now be illustrated by means of the following Examples which are provided for illustrative purposes and are not to be construed as limiting the invention.

ILLUSTRATIVE EMBODIMENTS

EXAMPLE 1

A 100 ml stainless steel autoclave was charged with 20 ml benzene, in which are dissolved 0.02 mmol of 1,5-cyclooctadiene-rhodium(I) acetate and 0.2 mmol of tris(2-t.butylphenyl)phosphite, under an atmosphere of argon and the autoclave was also charged with 10 mmol of 2-methylhex-1-ene. The autoclave was then pressurized with a 1:1 molar mixture of hydrogen and carbon monoxide and heated to 80° C., the pressure in the autoclave now being 14 bar. The autoclave was kept 1 hour at the reaction temperature of 80° C. and then cooled to ambient temperature. After venting the gases, the reaction product was analyzed using gas chromatography and NMR. The product obtained contained more than 95% of the desired linear aldehyde 3-methyl-n-heptanal. The rate of the hydroformylation of this less reactive 2-methyl-hex-1-ene, expressed in moles per mole rhodium per hour amounted to 1000.

EXAMPLE 2

The experiment described in the previous Example was repeated using a hydrogen:carbon monoxide ratio of 2:1 at a reaction temperature of 70° C. and a total pressure of 18 bar. The rate of the hydroformylation, expressed as defined in the previous Example, amounted to 1600. Again, more than 95% the desired aldehyde had been formed.

EXAMPLE 3

The experiment described in Example 1 was repeated using 0.2 mmol of tris(o-isopropylphenyl)phosphite under otherwise similar conditions. The rate of hydroformylation amounted to 300.

COMPARATIVE EXAMPLE A

The experiment described in Example 1 was repeated but using 0.2 mmol of tris-2-tolylphosphite under otherwise similar conditions. The rate of hydroformylation, expressed as defined in Example 1, amounted only to 30.

COMPARATIVE EXAMPLE B

The experiment described in Example 1 was repeated but using 0.2 mmol of tris(2,6-dimethylphenyl)phosphite under otherwise similar conditions. No hydroformylated product could be detected at all.

COMPARATIVE EXAMPLE C

The experiment described in Example 2 was repeated but using 0.2 mmol of the well-known ligand triphenylphosphine. The reaction temperature was 72° C. The rate of hydroformylation, expressed as defined in Example 1, amounted to only 50.

EXAMPLE 4

The autoclave described in Example 1 was charged with 20 ml benzene in which were dissolved 0.02 mmol 1,5-cyclooctadiene rhodium(I) acetate and 0.1 mmol of tris(2-t.butylphenyl)phosphite under an atmosphere of argon. Cyclohexene (15 mmol) was added. The autoclave was then pressurized with hydrogen and carbon monoxide in a 2:1 molar ratio and then heated to 70° C., the pressure in the autoclave now being 18 bar. After 1 hour the reaction mixture was worked up in the manner described in Example 1. The rate of hydroformylation, expressed in mole product per mole rhodium per hour, amounted to 660.

EXAMPLE 5

The experiment described in the previous Example was repeated using 0.2 mmol of tris(2-t.butylphenyl)phosphite. The reaction was carried out at a temperature of 90° C. The rate of hydroformylation, expressed as defined in the previous Example, amounted to 4000.

COMPARATIVE EXAMPLE D

The experiment described in Example 4 was repeated using varying amounts of triphenylphosphine (from 0.01 up to 0.08 mmol). The rate of hydroformylation, expressed as defined in Example 4, was always less than 25.

EXAMPLE 6

The autoclave described in Example 1 was charged with 20 ml benzene, in which was dissolved 0.02 mmol, 1,5-cyclooctadiene rhodium(II) acetate and 0.3 mmol of tris(2-t.butylphenyl)phosphite under an atmosphere of argon. Limonene (12 mmol of a 1/1 mixture of the 1-methyl and 2-methyl isomers as obtained from dimerizing isoprene) was added. The autoclave was then pressurized with hydrogen and carbon monoxide in a 2:1 molar ratio and then heated to 90° C., the pressure in the autoclave being 14 bar. After 1 hour, the reaction mixture was worked up as described in Example 1. The rate of hydroformylation, expressed as defined in Example 1, amounted to 3500.

EXAMPLE 7

The experiment described in the previous Example was repeated using 10 ml benzene and 0.2 mmol of tris(2-phenylphenyl)phosphite under otherwise similar conditions. Limonene (10 ml) was added and the reaction proceeded under a pressure of 10 bar; the hydrogen:carbon monoxide ratio being 2:1. The rate of hydroformylation, expressed as defined in Example 1, amounted to 1500.

COMPARATIVE EXAMPLE E

The experiment described in Example 6 was repeated but using triphenylphosphine in rather large excess (0.4 mmol). The rate of hydroformylation, expressed as defined in Example 6, amounted to 100.

EXAMPLE 8

The experiment described in Example 6 was repeated using natural limonene as the starting material (60 mmol) in half the amount of benzene in which the rhodium compound (0.03 mmol) had been dissolved together with 0.21 mmol of tris(2-t.butylphenyl)phosphite. The reaction temperature amounted to 80° C. The rate of hydroformylation, expressed as defined in Example 1, amounted to 1700.

EXAMPLE 9

The experiment described in Example 1 was repeated using methylenecyclohexane as the starting material. The reaction was carried out at a temperature of 75° C. and the total pressure amounted to 20 bar (hydrogen:

carbon monoxide 1:1). The rate of hydroformylation amounted to 3000.

EXAMPLE 10

In a two liter reactor were placed limonene (900 g), 1,5-cyclooctadiene rhodium(I) acetate (175 mg) and tris(2-t.butyl-4-methylphenyl)phosphite (17.0 g). A mixture of hydrogen and carbon monoxide (mol ratio 1:1) was introduced into the liquid while stirring, the pressure being kept at 15 bar. The reaction mixture was heated to 100° C. After 7 hours the reaction mixture was worked up. The limonene conversion was about 90% and the selectivity to aldehyde amounted to 90%. After removal of the product and the addition of fresh limonene to the reactor, the remaining catalytic solution could be used again.

We claim:

1. A process for the hydroformylation of olefins to aldehydes which comprises reacting at a temperature of from about 50° C. to about 200° C. and a pressure of from about 2 to about 50 bar an olefin containing the group

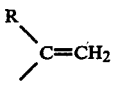

or the group

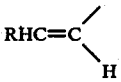

wherein R represents a hydrocarbyl group and the valence bond shown forms part of a hydrocarbyl group, or R together with the valence bond shown represents a ring structure having at least 5 carbon atoms in the ring, with carbon monoxide and hydrogen in the presence of a Group VIII-metal hydroformylation catalyst which has been modified by a ligand according to the general formula $$L(OR^1)(OR^2)(OR^3)$$

wherein L represents a phosphorus or arsenic moiety and $R^1$, $R^2$ and $R^3$ represent (dis)similar aryl groups provided that at least one of $R^1$, $R^2$ and $R^3$ represents a group

wherein Q represents a group

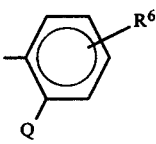

or a group

wherein each $R^4$ which may be the same or different represents an optionally fluorine-containing hydrocarbyl group, $R^5$ represents a hydrogen atom or a group $R^4$, $R^6$ represents a hydrogen atom or an inert substituent on the meta and/or para position of the ring, while X represents an oxygen or sulphur atom and n is 0 or 1, and $R^7$ represents a hydrogen atom or an inert substituent.

2. The process of claim 1 wherein the olefin is a β-alkyl substituted acyclic α-olefin.

3. The process of claim 2 wherein the olefin is 2-methylhex-1-ene.

4. The process of claim 1 wherein the olefin is a β-alkyl substituted acyclic α-olefin containing also a cyclic structure.

5. The process of claim 4 wherein the olefin is limonene.

6. The process of claim 1 wherein the olefin is a cyclic olefin having a methylene group in the molecule.

7. The process of claim 1 wherein the olefin is methylene cyclohexane.

8. The process of claim 1 wherein the olefin is a cyclic olefin having an unsubstituted double bond in the molecule.

9. The process of claim 8 wherein the olefin is cyclohexene.

10. The process of claim 1 wherein a catalyst is used which has been modified by a phosphite according to the general formula $L(OR^1)(OR^2)(OR^3)$ wherein at least one of the groups $R^1$, $R^2$ and $R^3$ represents an ortho-substituted phenyl group wherein $R^4$ represents a lower alkyl group, $R^5$ represents a hydrogen atom or a lower alkyl group, $R^6$ represents a hydrogen atom, a fluorine or chlorine atom, an alkyl or alkoxy group and n is 0 or 1 in which case X represents an oxygen or sulphur atom, and $R^7$ represents a hydrogen, fluorine or chlorine atom or a lower alkyl or alkoxy group.

11. The process of claim 10 wherein a catalyst is used which has been modified by a phosphite containing an ortho-substituted phenyl group wherein $R^4$ represents a methyl or ethyl group, $R^5$ represents a hydrogen atom or a methyl or ethyl group and n is 0, and $R^7$ represents a hydrogen atom.

12. The process of claim 11 wherein a catalyst is used which has been modified by tris(2-t.butylphenyl)-phosphite or tris(2-t.butyl-4-methylphenyl)phosphite.

13. The process of claim 1 wherein the phosphite according to the general formula $L(OR^1)(OR^2)(OR^3)$ is used in a metal:phosphorus ratio of from about 1:2 to about 1:100, preferably between 1:4 and 1:20.

14. The process of claim 1 wherein the process is carried out at a temperature in the range of from about 50° C. to about 200° C.

15. The process of claim 14 wherein the temperature is in the range of from about 80° C. to about 130° C.

16. The process of claim 1 wherein the process is carried out under a pressure between about 2 and about 50 bar.

17. The process of claim 16 wherein the pressure is between about 2 and about 50 bar.

18. The process of claim 1 wherein the process is conducted in the presence of an inert solvent.

19. The process of claim 18 wherein the inert solvent is an aromatic hydrocarbon, an ether, a ketone or a nitrile.

20. The process of claim 1 wherein a molar ratio of catalyst to olefin is used in the range of from about 1:10000 to about 1:10.

21. The process of claim 20 wherein the molar ratio of catalyst to olefin is in the range of from about 1:5000 to about 1:100.

22. The process of claim 1 wherein the Group VIII-metal catalyst is iridium or rhodium.

23. The process of claim 22 wherein the catalyst is rhodium.

* * * * *